United States Patent [19]

Warriner

[11] Patent Number: Plant 5,576

[45] Date of Patent: Oct. 22, 1985

[54] ROSE PLANT JACARET

[75] Inventor: William A. Warriner, Tustin, Calif.

[73] Assignee: Jackson & Perkins Company, Medford, Oreg.

[21] Appl. No.: 557,198

[22] Filed: Dec. 2, 1983

[51] Int. Cl.[4] ..... A01H 5/00

[52] U.S. Cl. ..... Plt./28

[58] Field of Search ..... Plt./28

*Primary Examiner*—James R. Feyrer

*Attorney, Agent, or Firm*—Klarquist, Sparkman, Campbell, Leigh & Whinston

[57] ABSTRACT

A floribunda rose variety having vigorous, productive plant growth, small and double red flowers having a definite fragrance, few thorns and resistance to mildew.

1 Drawing Figure

This present invention relates to a new and distinct variety of rose plant of the floribunda class which has originated by me by crossing an unnamed variety with the variety Caper, U.S. Plant Pat. No. 3,937.

The primary objective of this breeding was to produce a new rose variety combining the colors of both parents in a variety suitable for abundant production of small flowers usable as cut flowers. This objective was substantially achieved along with other desirable improvements as evidenced by the following unique combination of characteristics which are outstanding in the new variety and which distinguish it from its parents, as well as from all other varieties of which I am aware:

1. A vigorous, productive plant, freely branching to produce small red buds.
2. Open flowers are small, double (40 petals), red.
3. Definite fragrance.
4. Few thorns.
5. Resistance to mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Caper, U.S. Plant Pat. No. 3,937.

Classification:

*Botanical.*—Rosa hybrid.

*Commercial.*—Floribunda.

FLOWER

Observations made from specimens grown in a greenhouse at Irvine, Calif. in January.

Blooming habit: Continuous.

Bud:

*Size.*—Approximately $\frac{3}{4}''$ when petals start to unfurl.

*Form.*—Short, blunt top.

*Color.*—When sepals first divide, near Red 46A. When half blown, upper side of petals near Red 45A; lower side of petals near Red 45A.

*Sepals.*—Color: Outer surface Green 138A with smooth surface. Three appendaged sepals normally appendaged. Two unappendaged sepals hairy edged.

*Receptacle.*—Color: Green 138A. Shape: Funnel. Size; Small. Surface: Smooth.

*Peduncle.*—Length: Long. Surface: Slightly glandular. Color: Light green. Strength: Stiff, erect; slender.

*Opening.*—Petals curl slightly as they fold outward.

Bloom:

*Size.*—Small. Average open size: $1\frac{1}{2}''$.

*Borne.*—Singly or several together.

*Stems.*—Short, normal.

*Form.*—When first open, high centered. Permanence: All petals curl, quill fashion.

*Petalage.*—Number of petals under normal conditions: approximately 40.

*Color.*—Center of flower: Upper side of petals Red 45A; reverse side of petals Red 45A; base of petals have very small white dot at point of attachment. General tonality from a distance: Red 45A.

*Variegations.*—None.

*Discoloration.*—General tonality at end of first day: Red 45A. Third day: Red 45A.

*Fragrance.*—Moderate.

Petals:

*Texture.*—Thin.

*Shape.*—Broadly obovate.

*Form.*—Edges slightly quilled.

*Arrangement.*—Imbricated. Petaloids in center: few, large.

*Persistenc.*—Drop off cleanly.

*Lastingness.*—On the plant, long. As cut flower, long.

Reproductive parts:

*Anthers.*—Large, few. Color: Yellow. Arrangement: Mixed with petaloids.

*Filaments.*—Color: Reddish.

*Pollen.*—Lemon yellow.

*Styles.*—Color: Reddish.

*Stigmas.*—Color: Pink.

PLANT

Form: Bush.

Growth: Very vigorous, upright.

Foliage: Number of leaflets on normal mid-stem leaves: usully 5.

*Size.*—Small.

*Quantity.*—Normal.

*Color.*—New foliage: Green overlaid with Greyed Purple 184B. Old foliage: Normal medium green.

Leaflets:

*Shape.*—Oval pointed.

*Texture.*—Leathery on upper side.

*Edge.*—Serrated.

*Serration.*—Single, small.

*Petiole.*—Rachis: Color: Reddish. Underside: Few prickles.

*Stipules.*—Long, bearded.

*Disease resistance.*—Resistant to mildew under normal growing conditions at Irvine, Calif.; subject to blackspot at same location.

Wood:

*New wood.*—Color: Reddish. Bark: Smooth.

*Old wood.*—Color: Green. Bark: Smooth.

Prickles:

*Quantity.*—On main stalks from base: few. On laterals from stalk: few.

*Form.*—Long, straight.

*Color when young.*—Brown.

*Position.*—Irregular.

Small prickles:

*Quantity.*—On main stalks: none. On laterals: none.

I claim:

1. A new and distinct variety of rose plant of the floribunda class, substantially as herein shown and described, characterized particularly as to novelty by the unique combination of high production of small red buds; small, open blooms; fragrance; and a good degree of resistance to rose powdery mildew.

* * * * *

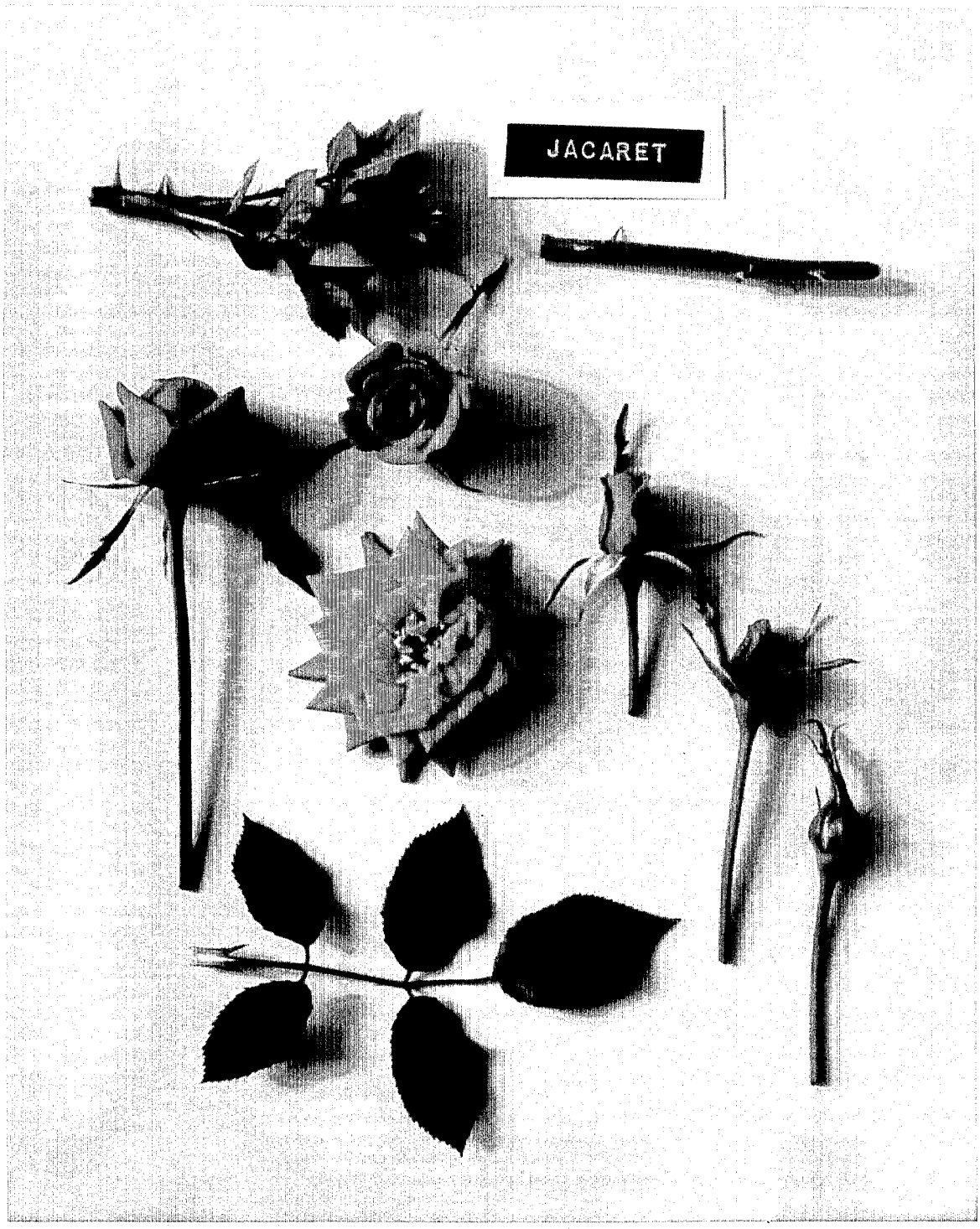
JACARET